US009586026B2

(12) United States Patent
Scandone, Jr. et al.

(10) Patent No.: US 9,586,026 B2
(45) Date of Patent: *Mar. 7, 2017

(54) CATHETER TUNNELER ADAPTER

(71) Applicant: MEDICAL COMPONENTS, INC., Harleysville, PA (US)

(72) Inventors: Charles Scandone, Jr., Malvern, PA (US); Mark S. Fisher, Sellersville, PA (US)

(73) Assignee: Medical Components, Inc., Harleysville, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/071,361

(22) Filed: Mar. 16, 2016

(65) Prior Publication Data

US 2016/0193451 A1 Jul. 7, 2016

Related U.S. Application Data

(63) Continuation of application No. 13/799,723, filed on Mar. 13, 2013, now Pat. No. 9,333,325.

(60) Provisional application No. 61/723,852, filed on Nov. 8, 2012.

(51) Int. Cl.
| *A61M 25/16* | (2006.01) |
| *A61M 25/01* | (2006.01) |
| *A61M 5/178* | (2006.01) |

(52) U.S. Cl.
CPC ........ *A61M 25/0194* (2013.01); *A61M 5/178* (2013.01); *A61M 2025/0197* (2013.01)

(58) Field of Classification Search
CPC .......... A61M 25/0194; A61M 25/0102; A61M 2039/062
USPC ............... 604/93.01, 508, 523, 535; 606/108
See application file for complete search history.

(56) References Cited

U.S. PATENT DOCUMENTS

| 6,969,381 | B2 | 11/2005 | Voorhees | |
|---|---|---|---|---|
| 7,128,734 | B1 | 10/2006 | Wilson et al. | |
| 7,261,708 | B2 | 8/2007 | Raulerson | |
| D562,443 | S | 2/2008 | Zinn et al. | |
| D575,393 | S | 8/2008 | Stephens | |
| D599,478 | S | 9/2009 | Bizup et al. | |
| 8,905,998 | B2 | 12/2014 | Stephens | |
| 2004/0092863 | A1 | 5/2004 | Raulerson et al. | |
| 2004/0176739 | A1* | 9/2004 | Stephens ............... | A61M 29/00 604/523 |
| 2005/0027282 | A1* | 2/2005 | Schweikert ........ | A61B 17/3415 604/523 |
| 2005/0261664 | A1 | 11/2005 | Rome et al. | |
| 2006/0009783 | A1* | 1/2006 | Rome ................ | A61B 17/3415 606/108 |

(Continued)

*Primary Examiner* — Nathan R Price
*Assistant Examiner* — Gerald Landry, II
(74) *Attorney, Agent, or Firm* — Fox Rothschild LLP

(57) ABSTRACT

A catheter tunneling adapter including a longitudinal body having a distal end and a proximal end and a passageway extending from an entrance at the proximal end to an exit at the distal end. The passageway has a first hemisphere and a second hemisphere with the first hemisphere defining a generally unobstructed first passageway portion from the entrance to the exit. A guide ramp is positioned within the second passageway and tapers towards the first hemisphere moving from the proximal end to the distal end. The ramp defines a longitudinal notch therethrough such that a second passageway portion extends from the entrance to the exit.

18 Claims, 6 Drawing Sheets

(56) References Cited

U.S. PATENT DOCUMENTS

| | | | |
|---|---|---|---|
| 2006/0015130 A1* | 1/2006 | Voorhees, Jr. | A61B 17/3415 606/190 |
| 2006/0135949 A1 | 6/2006 | Rome et al. | |
| 2007/0078396 A1 | 4/2007 | Feeley et al. | |
| 2007/0078478 A1 | 4/2007 | Atkins et al. | |
| 2007/0219510 A1 | 9/2007 | Zinn et al. | |
| 2007/0265597 A1* | 11/2007 | Schweikert | A61B 17/3415 604/533 |
| 2008/0097409 A1* | 4/2008 | Stephens | A61B 17/3415 604/533 |
| 2008/0214992 A1* | 9/2008 | Haarala | A61B 17/3415 604/44 |
| 2008/0300576 A1 | 12/2008 | Vitullo et al. | |
| 2008/0319421 A1 | 12/2008 | Bizup et al. | |
| 2009/0030426 A1 | 1/2009 | Zinn et al. | |
| 2010/0063512 A1* | 3/2010 | Braga | A61B 17/32 606/108 |
| 2010/0106094 A1 | 4/2010 | Fisher et al. | |
| 2012/0083794 A1 | 4/2012 | Martin et al. | |
| 2014/0128816 A1 | 5/2014 | Scandone, Jr. et al. | |

* cited by examiner

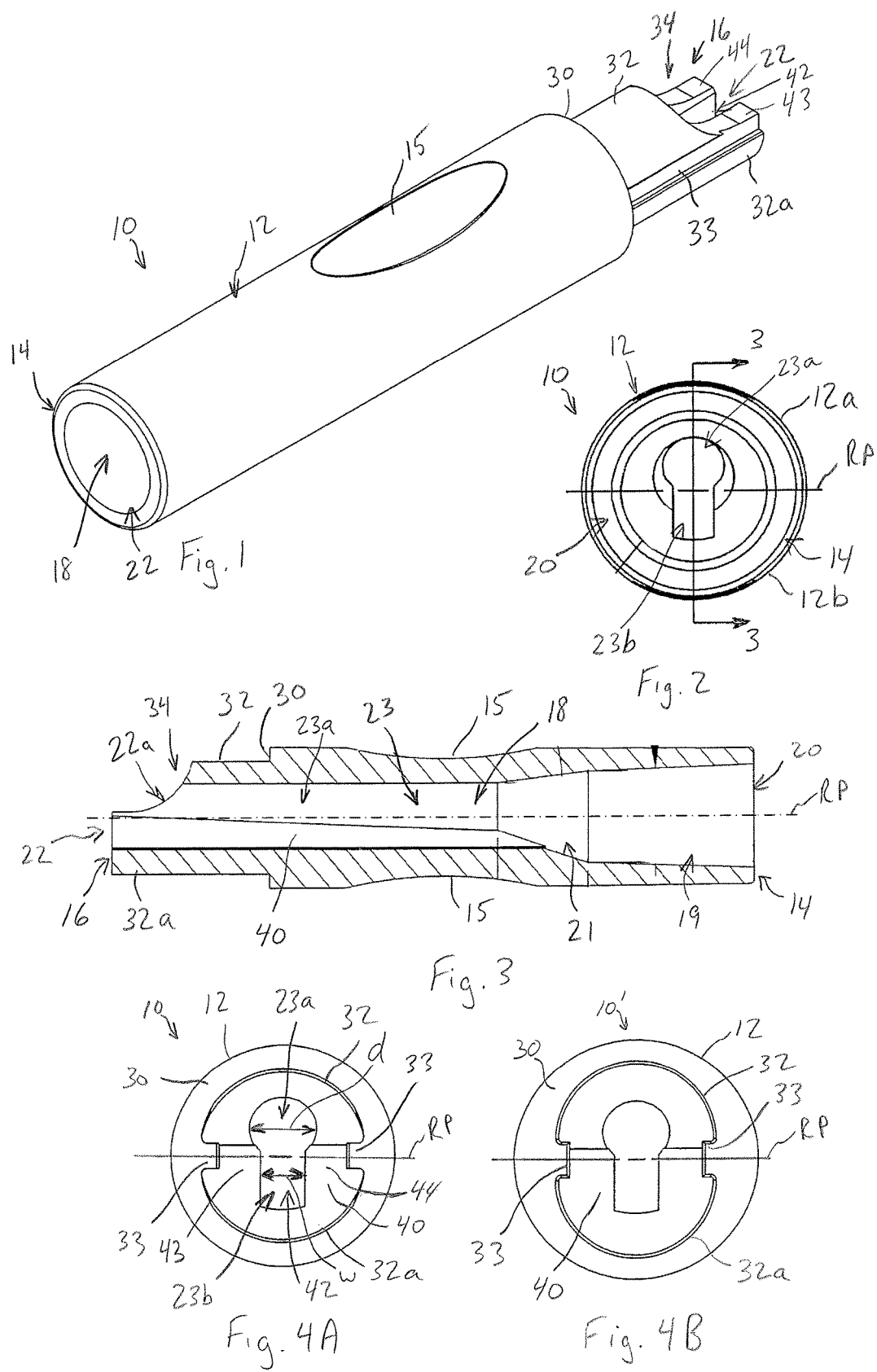

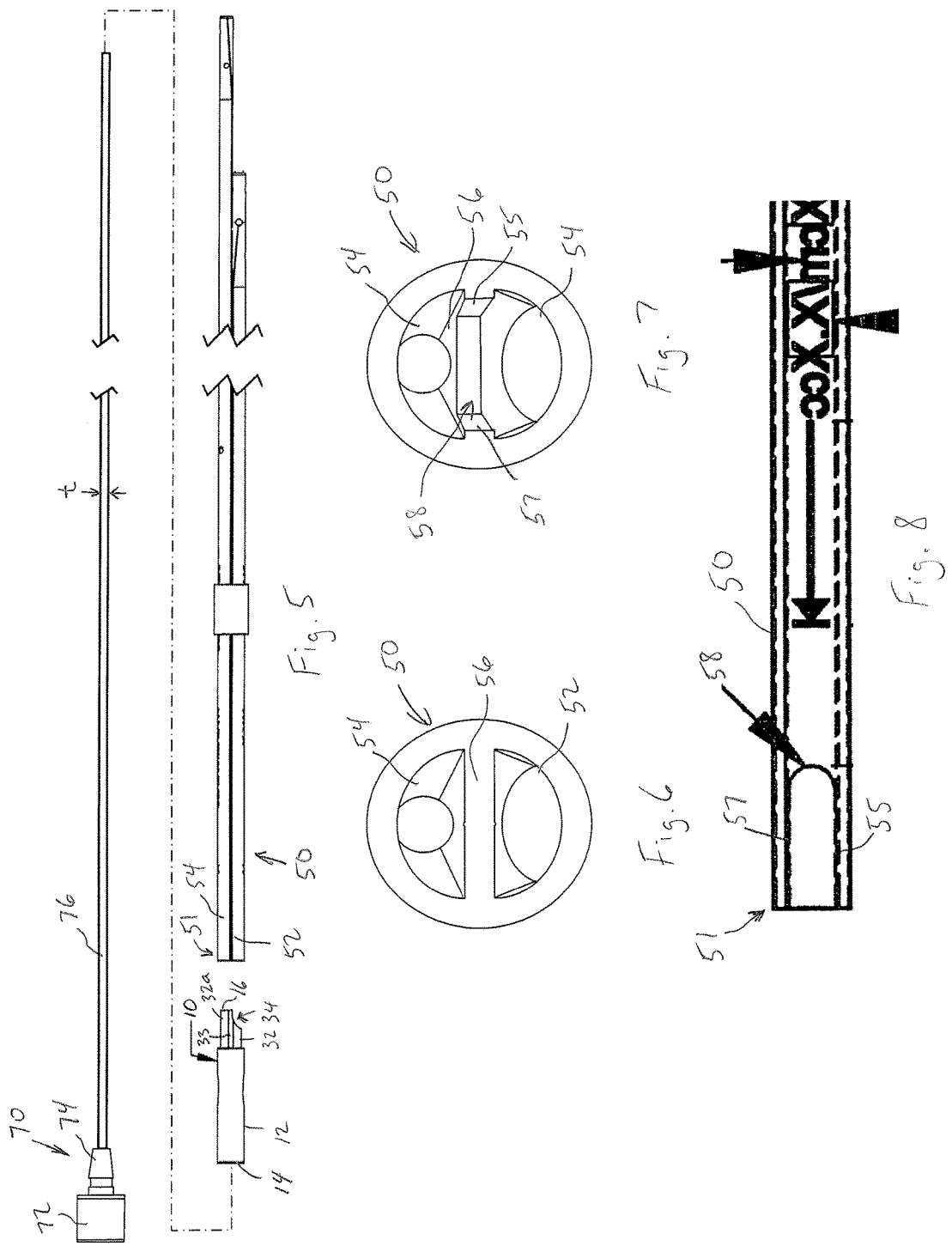

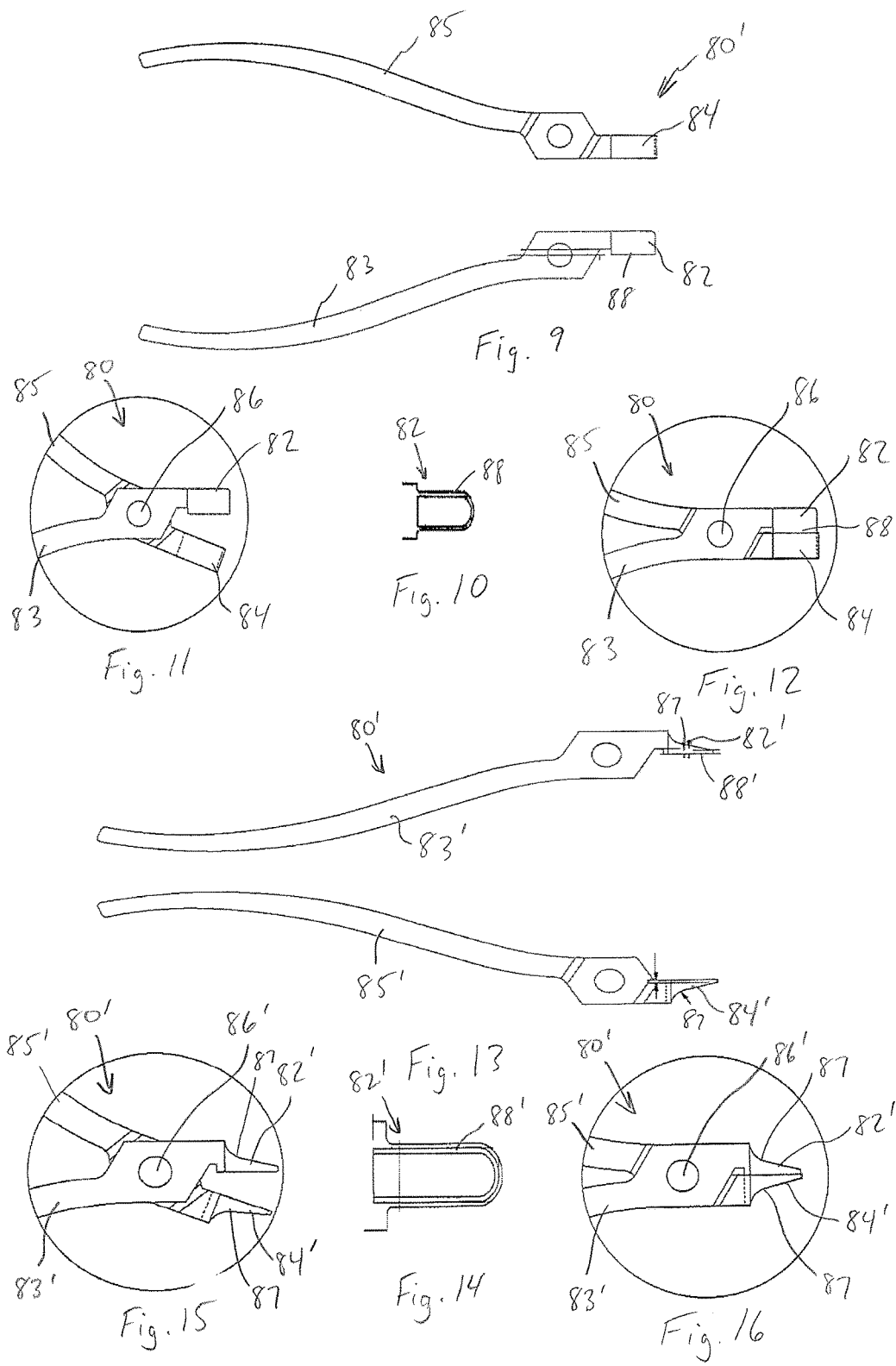

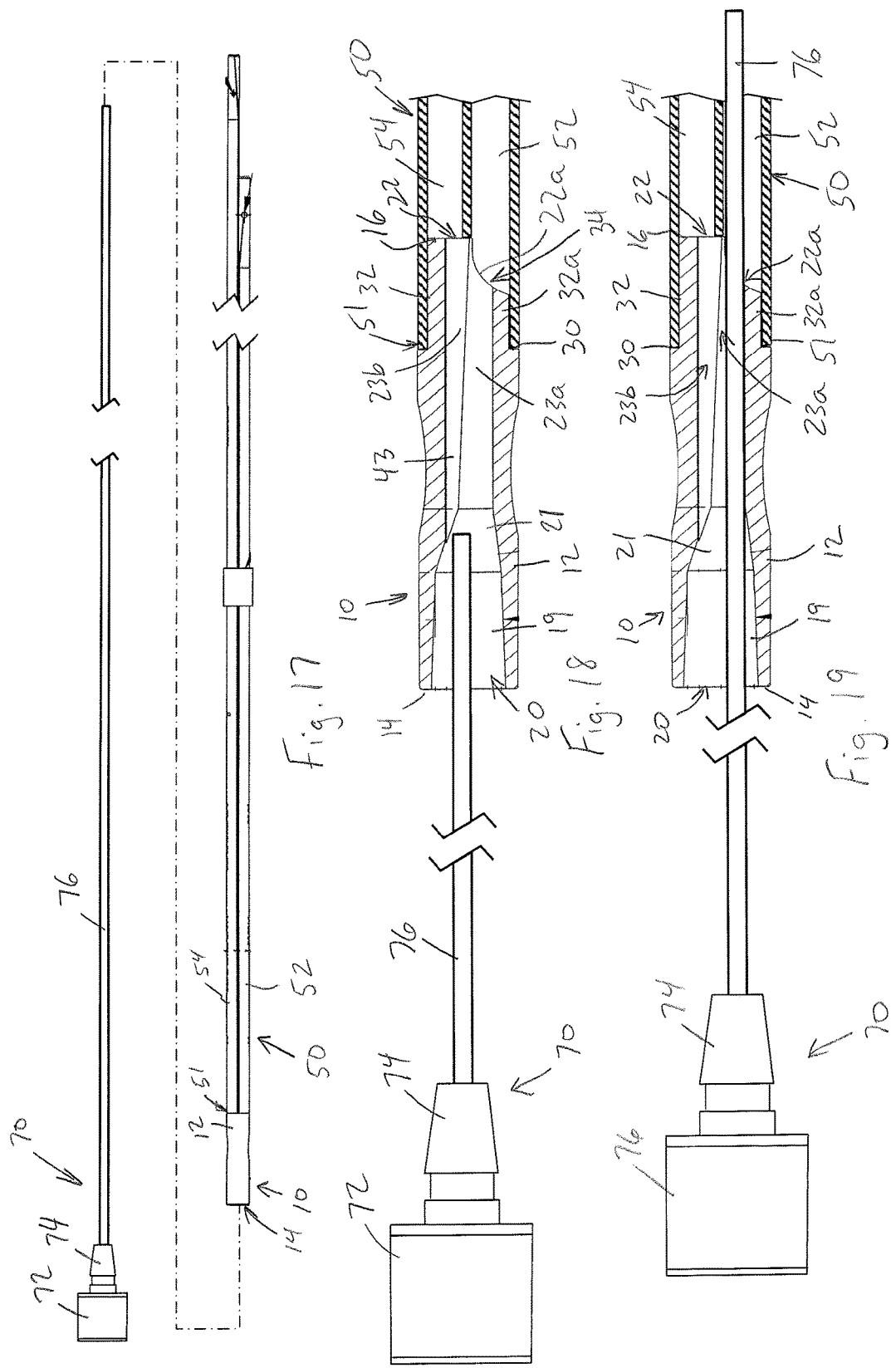

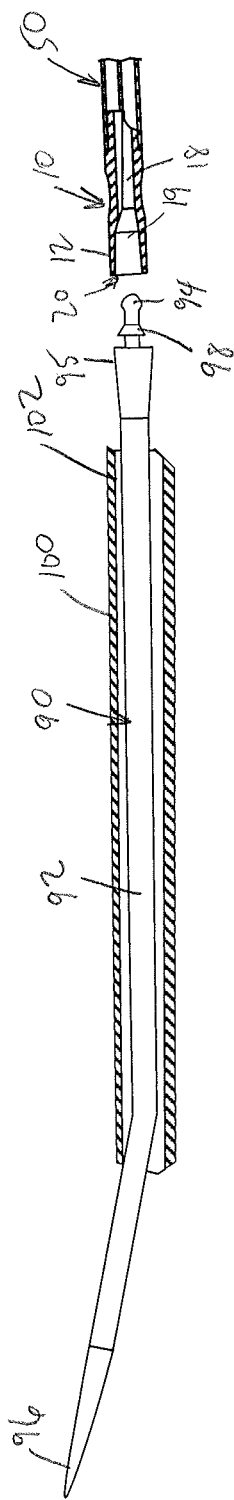
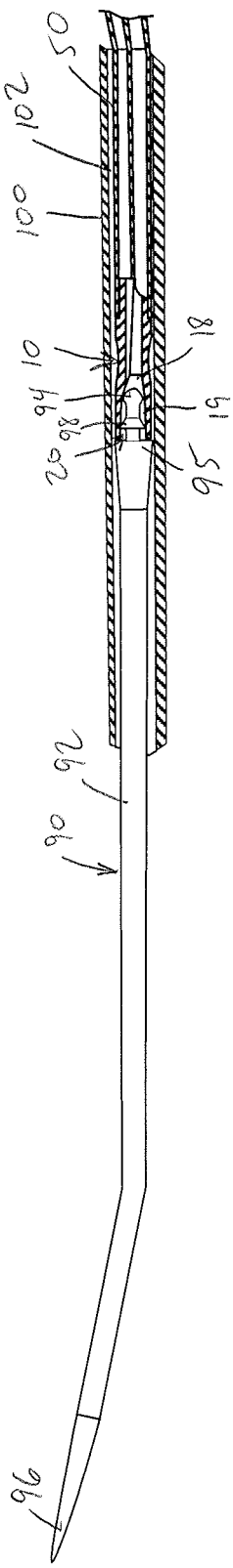
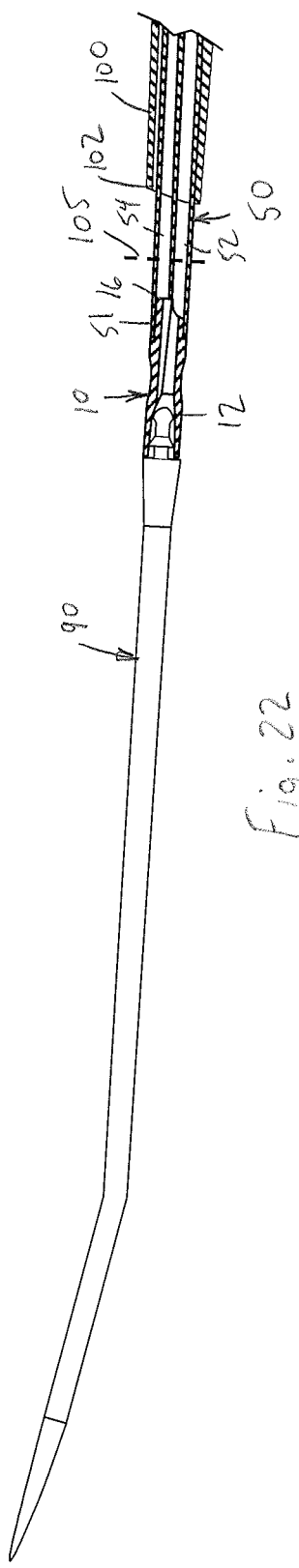
Fig. 20
Fig. 21
Fig. 22

CATHETER TUNNELER ADAPTER

This application is a continuation of U.S. patent application Ser. No. 13/799,723 filed Mar. 13, 2013, which application claims the benefit of U.S. Provisional Appln. No. 61/723,852 filed on Nov. 8, 2012, the contents of which are incorporated herein by reference.

FIELD OF THE INVENTION

This invention relates to medical devices and more particularly to an adapter for a vascular catheter to facilitate subcutaneous tunneling thereof.

BACKGROUND OF THE INVENTION

Catheters for the introduction or removal of fluids may be located in various venous locations and cavities throughout the body of a patient for introduction of fluids to the body or removal of fluids from the body. Such catheterization may be performed by using a single catheter having multiple lumens. A typical example of a multiple lumen catheter is a dual lumen catheter in which one lumen introduces fluid and the other lumen removes fluid. An example of such a multiple catheter is the SPLIT-CATH® catheter, sold by Medical Components, Inc. of Harleysville, Pa.

Generally, to insert any catheter into a blood vessel, the vessel is identified by aspiration with a long hollow needle in accordance with the well known Seldinger technique. When blood enters a syringe attached to the needle, indicating that the vessel has been found, a thin guide wire is then introduced, typically through a syringe needle or other introducer device into the interior of the vessel. The introducer device is then removed, leaving the end portion of the guide wire that has been inserted into the vessel within the vessel and the opposing end of the guide wire projecting beyond the surface of the skin of the patient. At this point, several options are available to a physician for catheter placement. The simplest is to pass a catheter into the vessel directly over the guide wire. The guide wire is then removed, leaving the catheter in position within the vessel. However, this technique is only possible in cases where the catheter is of a relatively small diameter, made of a stiff material, and not significantly larger than the guide wire. For example, this technique may be used to insert small diameter dual lumen catheters into a patient. If the catheter to be inserted is significantly larger than the guide wire, a dilator device is passed over the guide wire to enlarge the hole. The dilator device is then removed, and the catheter is then passed over the guide wire into the vessel. The guide wire is then removed.

For chronic catheterization, in which the catheter is intended to remain inside the patient for an extended period of time, such as for weeks or even months, it is typically desired to subcutaneously tunnel the catheter using various tunneling techniques. The catheter is typically tunneled into the patient prior to inserting the catheter into the patient's vein. However, depending on the patient or the implanting surgeon's skill, there may be times when it is more advantageous to perform the tunneling after the catheter is implanted in the patient. For some catheters, though, such as multiple lumen catheters with a hub and with bonded luers on the proximal ends of the catheters, it is impractical to perform the tunneling after the catheter is installed in the patient.

An alternative installation procedure is available for installing the catheter that better suits the patient's needs and the surgeon's skills. Such an alternative catheter assembly is the multi-lumen catheter disclosed in U.S. patent publication No. US 2004/0092863. In order to be able to perform the tunneling after the distal end of the catheter assembly is inserted into the patient (termed retrograde tunneling), the proximal ends of each catheter must be attached to a tunneler device adapted to pull the proximal end of each catheter through the tunnel. After tunneling, the proximal ends of the catheters must be disconnected from the tunneler device and then connected to a catheter hub.

U.S. patent publication Nos. US 2004/0176739 and 2008/0097409, incorporated by reference, each describe a catheter tunneling adapter that allows for the simultaneous tunneling of the proximal ends of each catheter in a multi-lumen catheter assembly. In each case, the adapter is comprised of a generally elongated body having a distal end and a proximal end and a longitudinal axis extending therethrough between the distal end and the proximal end. The proximal end includes a connector for connecting a catheter tunneler thereto. The distal end comprises a connector for connecting a plurality of catheter lumens thereto. The publications also provide a method of inserting a catheter having a plurality of lumens into a patient. The method is comprised of inserting a distal end of each of the plurality of lumens into a blood vessel in the patient; connecting a proximal end of each of the plurality of lumens to a tunneling device; forming a subcutaneous tunnel with the tunneling device; drawing the proximal ends of each of the plurality of lumens simultaneously through the tunnel; disconnecting the tunneling device from the proximal ends of each of the plurality of lumens; and connecting the proximal ends of each of the plurality of lumens to a catheter hub component. Such a catheter hub component may be as disclosed in U.S. Pat. No. 7,261,708 or 6,969,381, each of which discloses a hub that is mountable to a catheter's proximal end after tunneling thereof has been performed.

SUMMARY OF THE INVENTION

The present invention is an adapter that at its distal end is securable onto the ends of two (or more) lumens of a catheter to facilitate implantation thereof in a patient's vasculature, and is securable at its proximal end to, sequentially, a flushing syringe, a stylet and also a tunneler, so that while connected to the catheter's proximal end it permits releasable connection with a stylet for the guide wire to permit implantation of the distal portion in place in the vasculature, and then with a tunneler for subcutaneous tunneling of the proximal portion of the catheter. In at least one embodiment, the catheter tunneling adapter includes a longitudinal body having a distal end and a proximal end and a passageway extending from an entrance at the proximal end to an exit at the distal end. The passageway has a first hemisphere and a second hemisphere with the first hemisphere defining a generally unobstructed first passageway portion from the entrance to the exit. A guide ramp is positioned within the second passageway and tapers towards the first hemisphere moving from the proximal end to the distal end. The ramp defines a longitudinal notch therethrough such that a second passageway portion extends from the entrance to the exit.

In at least one embodiment, the passageway entrance is configured to receive a portion of a syringe and a fluid expelled from the syringe passes through and exits both the first and second passageway portions at the distal end of the longitudinal body.

In at least one embodiment, the adapter is adapted for use with a catheter including first and second lumens and the first passageway portion is aligned with the first lumen and the second passageway portion is aligned with the second lumen. Furthermore, the passageway is configured for passage of a stylet shaft having a given outer diameter therethrough, and the diameter of the first passageway portion is greater than the given outer diameter and the width of the second passageway portion is less than the given outer diameter. In at least one embodiment, the passageway entrance is configured to receive a portion of a syringe and a fluid expelled from the syringe passes through the first passageway portion and flows into the first lumen and also passes through the second passageway portion and into the second lumen.

BRIEF DESCRIPTION OF THE DRAWINGS

The accompanying drawings, which are incorporated herein and constitute part of this specification, illustrate the presently preferred embodiments of the invention, and, together with the general description given above and the detailed description given below, serve to explain the features of the invention. In the drawings:

FIG. 1 is an isometric view of an exemplary adapter in accordance with an embodiment of the present invention, FIG. 2 is a proximal end view of the adapter of FIG. 1.

FIG. 3 is a cross-sectional view along the line 3-3 in FIG. 2.

FIGS. 4A and 4B are distal end views of exemplary embodiments of the adapter of FIG. 1.

FIG. 5 is an exploded side view illustrating the adapter of FIG. 1 prior to assembly with a catheter and a stylet.

FIG. 6 is a proximal end view of the catheter of FIG. 5 prior to assembly preparation.

FIG. 7 is a proximal view similar to FIG. 6 illustrating the catheter proximal end after it has been prepared for assembly in accordance with an exemplary embodiment of the invention.

FIG. 8 is a partial top plan view of the catheter proximal end after assembly preparation.

FIG. 9 is an exploded view of an exemplary cutting tool for preparation of the catheter proximal end in accordance with an exemplary embodiment of the invention.

FIG. 10 is a partial plan view of a cutting surface of one of the jaws of the cutting tool of FIG. 9.

FIG. 11 is a side elevation view of the cutting tool of FIG. 9 in an open position.

FIG. 12 is a side elevation view of the cutting tool of FIG. 9 in a closed position.

FIG. 13 is an exploded view of another exemplary cutting tool for preparation of the catheter proximal end in accordance with an exemplary embodiment of the invention.

FIG. 14 is a partial plan view of a cutting surface of one of the jaws of the cutting tool of FIG. 13.

FIG. 15 is a side elevation view of the cutting tool of FIG. 13 in an open position.

FIG. 16 is a side elevation view of the cutting tool of FIG. 13 in a closed position.

FIG. 17 is an exploded side view illustrating the adapter of FIG. 1 assembled with a catheter and prior to insertion of a stylet.

FIG. 18 illustrates initial insertion of the stylet into the adapter and catheter assembly, which are shown in longitudinal cross-section.

FIG. 19 is a view similar to FIG. 18 illustrating the stylet further inserted into the adapter and catheter assembly.

FIGS. 20-22 are schematic views illustrating sequentially an exemplary tunneling procedure using the adapter of FIG. 1.

DETAILED DESCRIPTION OF THE INVENTION

Figure 23:
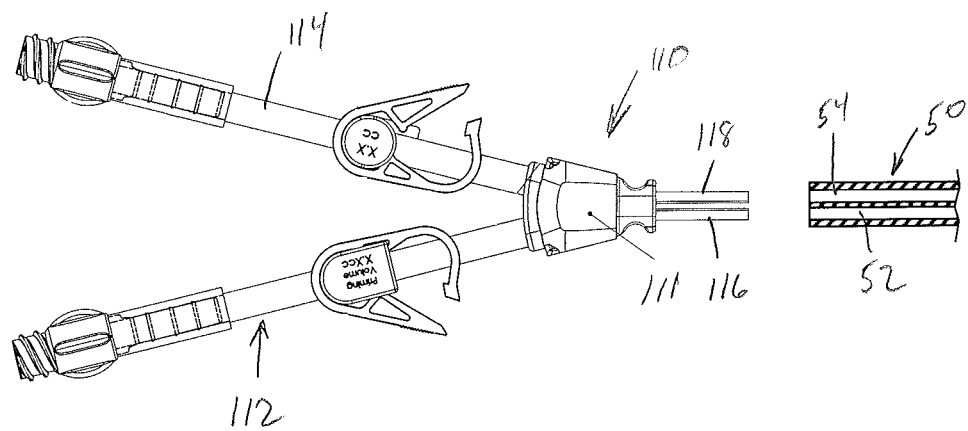
FIG. 23 is a top plan view illustrating the catheter proximal end prior to assembly with an exemplary hub.

In the drawings, like numerals indicate like elements throughout. Certain terminology is used herein for convenience only and is not to be taken as a limitation on the present invention. The words "proximal" and "distal" refer to directions away from and closer to, respectively, the insertion tips of a catheter adapted to connect to the adapter of the present invention. The terminology includes the words above specifically mentioned, derivatives thereof, and words of similar import. The following describes a preferred embodiment of the invention. However, it should be understood based on this disclosure, that the invention is not limited by the preferred embodiment described herein.

An adapter 10 in accordance with an exemplary embodiment of the present invention is shown in FIGS. 1 to 5. The adapter 10 includes a body 12 having a proximal end 14, a distal end 16, and a through passageway 18 extending through the body 12 from an entrance 20 at the proximal end 14 to an exit 22 at the distal end 16. Recesses 15 may be provided along the outer surface of the adapter body 12 to assist in gripping the adapter 10. While the adapter body 12 is preferably formed as a unitary annular body about the passageway 18, a reference plane RP is illustrated in the drawings and the body will be described with respect to a first hemisphere 12a and a second hemisphere 12b for clarity of description. While the reference plane RP is illustrated passing through a central axis of the body 12, it may be closer to the first hemisphere 12a or the second hemisphere 12b depending on the configuration of the catheter 50 with which the adapter 10 is to be used. In this way, the first hemisphere 12a and the second hemisphere 12b do not have to be equivalent and one may have a larger volume than the other and may have a greater inner or outer surface area. It is preferable that the adapter 10 is made of soft biocompatible material like polyurethane, such as, for example, PELLETHANE® polyurethane sold by Dow Chemical Co. of Midland, Mich. and having a durometer such as about 80A, however, other material may be utilized.

The distal end 16 of the adapter body 12 includes a radially inward step 30 which defines a reduced diameter annular connection surface 32 about the distal end of the passageway 18. The connection surface 32 is configured to be received in the proximal end of a double lumen catheter 50 (see FIGS. 5 and 18). Referring to FIGS. 4A and 4B, longitudinal grooves 33 extend along each side of the annular surface 32 from the distal end 16 to the step 30. The illustrated grooves 33 are configured to receive remaining portions 55, 57 of the lumen divider 56 as will be described hereinafter. Accordingly, the grooves 33 are positioned relative to the reference plane RP to correspond to the configuration of the catheter 50 with which the adapter 10 is to be utilized. Furthermore, as illustrated by comparing the adapters 10, 10' in FIGS. 4A and 4B, the configuration of the adapter body 12, the step 30, the connection surface 32, 32a and the guide ramp 40, to be described below, may all be modified to correspond to the configuration of the catheter. For example, the adapter 10 of FIG. 4A is configured to be utilized with a 15.5 french TITAN® catheter while the adapter 10' of FIG. 4B is configured to be utilized with a 16 french SPLIT-CATH® catheter, both sold by Medical Components, Inc. of Harleysville, Pa.

As indicated at 34 in FIGS. 1 and 3, the portion of the connection surface 32 in the first hemisphere 12*a* is cut away immediately proximate the body distal end 16 such that the distal portion 32*a* of the connection surface 32 is generally semi-annular extending primarily in the second hemisphere 12*b*, although some of the connection surface distal portion 32*a* may extend into the first hemisphere 12*a*. In view of the cut away portion, the passageway 18 exits the body 12 in the first hemisphere 12*a* at radial exit 22*a* prior to the surface of the distal end 16.

Referring now to FIG. 3, the through passageway 18 includes a connection portion 19 extending from the entrance 20. The connection portion 19 is configured for connection to various medical devices as will be described in more detail hereinafter. The connection portion 19 preferably has a slight taper to assist with such connection. A transition portion 21 tapers from the connection portion 19 to a communication portion 23 which extends to the exit 22.

As will be described in more detail below, the passageway 18 facilitates flushing of both lumens 52, 54 of a catheter 50 with saline or the like, guides positioning of a stylet 70 into the catheter 50, and provides a connection to a tunneler or the like. With reference to FIG. 5, an exemplary stylet 70 includes a hub 72 from which extends an engagement projection 74 and a relatively stiff, elongate stylet shaft 76 sufficiently long to extend completely through a first lumen 52 of the catheter 50 and beyond its distal tip. As is known in the art, the stylet 70 allows a guide wire (not shown) to be easily insertablde through the stylet and thus through the adapter and the catheter, for use in vascular placement of the catheter's distal portion. During use, the frustoconical engagement projection 74 enters into the adapter's entrance 20 and is preferably frictionally engaged within the connection portion 19 for releasable connection with the adapter 10.

To ensure the stylet shaft 76 extends into the first lumen 52 and not the second lumen 54, a guide ramp 40 is defined in the passageway 18, generally in the second hemisphere 12*b*. The guide ramp 40 tapers radially inward beginning from the transition portion 21 and extending through the second hemisphere 12*b* of the communication portion 23 to the exit 22. With the guide ramp 40 generally in the second hemisphere 12*b*, the communication portion 23*a* in the first hemisphere 12*a* is defined as a generally circular cross-section with a diameter d (see FIG. 4A). The diameter d is greater than an outer diameter t of the stylet shaft 76 (see FIG. 5) to be used with the adapter 10 such that the stylet shaft 76 can pass through the first hemisphere communication portion 23*a*. Configurations other than circular cross-section may be utilized provided a desired stylet shaft may pass through the first hemisphere communication portion 23*a*.

The guide ramp 40 includes a notch 42 extending the length thereof between opposed ramp sides 43 and 44. The notch 42 has a width w and defines the second hemisphere communication portion 23*b*. The width w is less than the outer diameter t of the stylet shaft 76 such that the stylet shaft 76 can not pass through the second hemisphere communication portion 23*b*, but instead contacts the ramp sides 43 and 44 and is directed to the first hemisphere communication portion 23*a* as shown in FIGS. 18 and 19. As will be described in more detail below, the first hemisphere communication portion 23*a* is aligned with a first catheter lumen 52 while the second hemisphere communication portion 23*b* is aligned with the second catheter lumen 54. As such, the configuration of the ramp 40 ensures that the stylet shaft 76 will always be directed to the first catheter lumen 52. Preferably the adapter 10 is positioned relative to the catheter 50 such that the first catheter lumen 52 is the arterial lumen, however, the adapter may be alternatively positioned such that the first lumen 52 is the venous lumen.

Referring to FIGS. 5-8, the catheter 50 defines the first and second lumens 52, 54 with a lumen divider 56 between the two lumens 52, 54. The catheter 50 is preferably manufactured using a drawing technique although other methods may be utilized. FIG. 6 illustrates the catheter 50 after manufacture with the lumen divider 56 extending to the proximal end 51 of the catheter 50. To receive the distal end 16 of the adapter 10, a portion of the lumen divider 56 must be removed to define a receiving notch 58 within the catheter proximal end 51. Preferably, the center portion of the divider 56 is removed while remaining portions 55, 57 extend along each side of the notch 58. The remaining portions 55, 57 are received in the respective grooves 33 of the adapter body 12 and help to ensure alignment of the adapter 10 relative to the catheter 50.

While the receiving notch 58 may be formed in the proximal end 51 of the catheter 50 during the forming process, FIGS. 9-16 illustrate a pair of exemplary tools 80, 80' which may be utilized to form the receiving notch 58 after the catheter 50 is formed but prior to assembly with the adapter 10. Each of the tools 80, 80' include opposed jaws 82, 82' and 84, 84' which are pivotal relative to each other about pivot point 86, 86'. In the illustrated embodiments, the jaws 82, 82' extend from handles 83, 83' and the jaws 84, 84' extend from handles 85, 85' such that the jaws may be manually pivoted relative to one another, however, other mechanism, for example automated machines, may be utilized to pivot the jaws relative to one another. In each jaw pair, one of the jaws 82, 82' includes an extending cutting edge 88 while the other jaw 84, 84' includes a corresponding recess (not shown). The cutting edge 88 has a shape corresponding to the desired shape of the receiving notch 58. To make the notch 58, the jaws 82, 84; 82', 84' are positioned within the proximal end 51 of the catheter 50 in an open position as shown in FIGS. 11 and 15. In this way, the jaw 82, 82' will enter the first lumen 52 and the jaw 84, 84' will enter the second lumen 54 with the divider 56 between the jaws. The jaws 82' and 84' include a recessed back 87 to facilitate positioning with the lumens. Once positioned, the jaws 82, 84; 82', 84' are pivoted to the closed position shown in FIGS. 12 and 16 and the cutting edge 88, 88' passes through the lumen divider 56 and defines the notch 58. Other devices may alternatively be utilized to define the notch 58.

Referring to FIGS. 17-18, once the receiving notch 58 is defined in the proximal end 51 of the catheter 50, the distal end 16 of the adapter body 12 is positioned within the catheter 50 until the catheter 50 engages the step 30. The catheter 50 extends about the connection surface 32, 32*a* and is preferably secured thereto via bonding, welding, adhering or any other desired manner. As explained above, the interaction of the divider remaining portions 55, 57 and the grooves 33 will provide a rotational alignment feature. The adapter 10 only has to be oriented properly such that the first hemisphere communication portion 23*a* is aligned with the first lumen 52 and the second hemisphere communication portion 23*b* is aligned with the second lumen 54. The cutaway 34 defining the radial exit 22*a* may be utilized to assist with such alignment.

With the adapter 10 secured to the proximal end 51 of the catheter 50, the assembly is ready for use. Prior to insertion of the stylet 70, it is typical procedure to flush both lumens 52, 54 of the catheter 50. The adapter 10 facilitates easy flushing of both lumens 52, 54. A tip of a syringe or the like (not shown) is positioned through the entrance 20 of the passageway 18 into the connection portion 19. Since the first hemisphere communication portion 23a is aligned with the first lumen 52 and the second hemisphere communication portion 23b is aligned with the second lumen 54, the flushing fluid that is dispensed into the passageway 18 simultaneously enters both lumens 52, 54 at a substantially similar flow rate.

Once flushing is complete and the syringe is removed, the stylet shaft 76 is positioned through the entrance 20 and into the passageway 18 as illustrated in FIG. 18. The taper of the transition portion 21 helps to generally guide the stylet shaft 76 toward the central axis of the passageway 18. If the stylet shaft 76 is directed toward the second hemisphere communication portion 23b, it will not be able to fit into the ramp notch and instead will be guided by the ramp sides 43, 44 toward the first hemisphere communication portion 23a. Once aligned with the first hemisphere communication portion 23a, the stylet shaft 76 passes through the radial outlet 22a and into the first lumen 52. The stylet shaft 76 is passed until it exits the lumen 52 and the hub projection 74 is receiving in the connection portion 19 of the adapter passageway 18. The distal end of the catheter 50 is then inserted into the vasculature by use of the stylet 70 in a known manner.

Once positioned, the stylet 70 is removed and discarded, and the proximal end 51 of the catheter assembly may be tunneled using a tunneler 90. Referring to FIG. 20, an exemplary tunneler 90 is shown after having been tunneled subcutaneously in a patient 100 to define a tunnel 102 prior to connection to adapter 10. The exemplary tunneler 90 has a rigid shaft 92 extending from a blunt tunneling tip 96 to a blunt connection tip 94 adjacent to which is a connection section 98 having a plurality of barbs or annular projections that could be used to connect to a catheter lumen directly, but are also useful in establishing a firm connection with adapter 10. Other types of tunnelers, for example, the Raulerson Ring Handled Y Adapter Tunneler sold by Medical Components, Inc. of Harleysville, Pa. may be utilized.

The tunneler 90 is connected to the adapter 10 by inserting the connection section 98 into proximal entrance 20 of adapter 10. The connection section 98 engages the adapter body 12 within the connection portion 19 of the passageway 18. The connection section 98 may form a fairly permanent connection with the adapter 10 as the adapter 10 will be cut from the catheter 50 after tunneling as described below. Once connected to the adapter 10, the tunneler 90 is pulled back through the tunnel 102 as shown in FIG. 21, thereby pulling the adapter 10 and catheter 50 proximal end 51 through tunnel 102. Preferably the adapter body 12 has a proximal end diameter which is equal to or less than the outer diameter of a guiding wedge 95 on the distal end of the tunneler 90. Similarly, the outer diameter of the adapter body 12 at the step 30 is greater than or equal to an outer diameter of the proximal end 51 of the catheter 50. In this way, the adapter 10 and catheter 50 are less likely to snag within the tunnel 102.

Referring to FIG. 22, after tunneling is completed, the proximal end 51 of the catheter 50 is cut at 105 distally of the distal end 16 of the adapter 10. The cut 105 is preferably perpendicular to the axis of the catheter 50. As illustrated, a single cut 105 will simultaneously leave two even lumens 52, 54. The severed portion of the catheter 50 and the adapter 10 may be discarded along with the tunneler 90.

Figure 24:
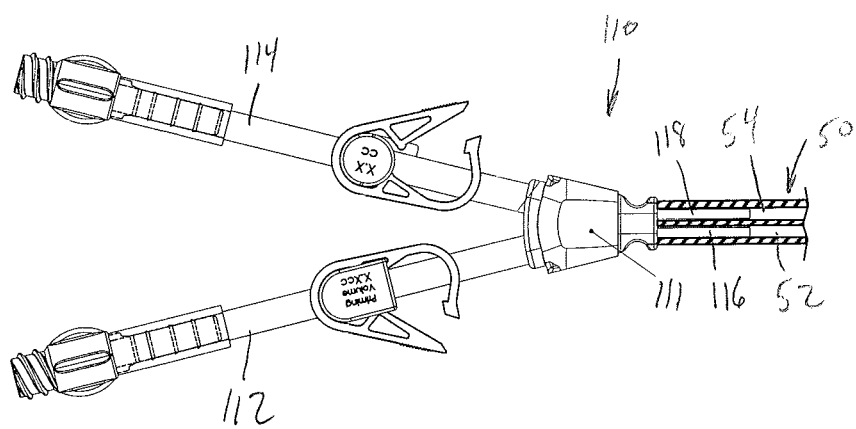
FIG. 24 is a view similar to FIG. 23 illustrating the catheter proximal end assembled with an exemplary hub.

Referring to FIGS. 23 and 24, connection of the catheter 50 to an exemplary hub assembly 110 will be described. The exemplary hub assembly 110 is similar to that described in U.S. Pat. No. 6,969,381. The hub assembly 110 includes a pair of extension tube assemblies 112 and 114 extending proximally from a hub base 111. The hub base 11a fluidly connects each extension tube assembly 112, 114 with a respective distally extending cannula 116, 118. Each cannula 116, 118 is configured to be received into a respective lumen 52, 54. The lumens 52, 54 are secured the hub base 111 via a clamp assembly (not shown) which is positioned over the catheter 50 and hub base 111.

It will be appreciated by those skilled in the art that changes could be made to the embodiment described above without departing from the broad inventive concept thereof. It is understood, therefore, that this invention is not limited to the particular embodiment disclosed, but it is intended to cover modifications within the spirit and scope of the present invention as defined by the appended claims.

What is claimed is:

1. A catheter tunneling adapter comprising: a longitudinal body having a distal end and a proximal end and a passageway extending from an entrance at the proximal end to an exit at the distal end, the distal end including a radially inward step which defines a contact surface configured to be received in a proximal end of a catheter, the passageway having a first hemisphere and a second hemisphere, with the first hemisphere defining a generally unobstructed first passageway portion from the entrance to the exit; and a guide ramp positioned within the second passageway and tapered towards the first hemisphere moving from the proximal end to the distal end, the ramp defining a longitudinal notch therethrough such that a second passageway portion extends from the entrance to the exit.

2. The catheter tunneling adapter according to claim 1, wherein the first passageway portion has a diameter greater than a width of the second passageway portion.

3. The catheter tunneling adapter according to claim 1, wherein the passageway entrance is configured to receive a portion of a syringe and a fluid expelled from the syringe passes through and exits both the first and second passageway portions at the distal end of the longitudinal body.

4. The catheter tunneling adapter according to claim 1, wherein the passageway entrance is configured to securably receive a distal end of a tunneler.

5. The catheter tunneling adapter according to claim 1, wherein a portion of the contact surface adjacent the first hemisphere is cutaway to define a radial exit.

6. The catheter tunneling adapter according to claim 1, wherein opposed grooves are defined in the contact surface from the distal end of the longitudinal body to the radially inward step.

7. The catheter tunneling adapter according to claim 1, wherein an outer surface of the longitudinal body defines one or more gripping recesses.

8. The catheter tunneling adapter according to claim 1, wherein a reference plane separating the first and second hemispheres passes through a central axis of the passageway.

9. The catheter tunneling adapter according to claim 1, wherein a reference plane separating the first and second hemispheres does not pass through a central axis of the passageway but instead is closer to the portion of the longitudinal body defining the first or second hemisphere.

10. The catheter tunneling adapter according to claim 1, wherein the entrance of the passageway is configured to receive and connect with a connection portion of a tunneler.

11. An assembly comprising: a catheter extending from a proximal end to a distal end and defining first and second lumens; and a tunneling adapter including a longitudinal body having a distal end and a proximal end and a passageway extending from an entrance at the proximal end to an exit at the distal end, the passageway having a first hemisphere and a second hemisphere, with the first hemisphere defining a generally unobstructed first passageway portion from the entrance to the exit, the longitudinal body distal end secured within the catheter proximal end; and a guide ramp positioned within the second passageway and tapered towards the first hemisphere moving from the proximal end to the distal end, the ramp defining a longitudinal notch therethrough such that a second passageway portion extends from the entrance to the exit wherein the first and second lumens are separated by lumen divider, and wherein a proximal portion of the lumen divider is omitted to define an adapter receiving notch configured to receive the distal end of the longitudinal body.

12. The assembly according to claim 11, wherein the first passageway portion is aligned with the first lumen and the second passageway portion is aligned with the second lumen.

13. The assembly according to claim 12, wherein the first lumen is an arterial lumen and the second lumen is a venous lumen.

14. The assembly according to claim 11, wherein the passageway is configured for passage of a stylet shaft having a given outer diameter therethrough, wherein the diameter of the first passageway portion is greater than the given outer diameter and the width of the second passageway portion is less than the given outer diameter.

15. The assembly according to claim 11, wherein the passageway entrance is configured to receive a portion of a syringe and a fluid expelled from the syringe passes through the first passageway portion and flows into the first lumen and also passes through the second passageway portion and into the second lumen.

16. The assembly according to claim 11, wherein the distal end of the longitudinal body includes a radially inward step which defines a contact surface which is received in receiving notch and the proximal end of the catheter contacts the step.

17. The assembly according to claim 16, wherein opposed side portions of the proximal lumen divider extend along the receiving notch and are received in opposed grooves defined in the contact surface from the distal end of the longitudinal body to the step.

18. The assembly according to claim 16, wherein an outer diameter of the longitudinal body at the step is greater than or equal to an outer diameter of the proximal end of the catheter.

\* \* \* \* \*